United States Patent
Brenizer et al.

(10) Patent No.: US 10,751,514 B2
(45) Date of Patent: Aug. 25, 2020

(54) GUIDE EXTENSION CATHETER

(71) Applicant: Teleflex Life Sciences Limited, Valletta, MT (US)

(72) Inventors: Joshua Brenizer, Maple Grove, MN (US); Dean Peterson, Minneapolis, MN (US)

(73) Assignee: Teleflex Life Sciences Limited, Valletta (MT)

( * ) Notice: Subject to any disclaimer, the term of this patent is extended or adjusted under 35 U.S.C. 154(b) by 409 days.

(21) Appl. No.: 15/581,176

(22) Filed: Apr. 28, 2017

(65) Prior Publication Data
US 2018/0161547 A1    Jun. 14, 2018

Related U.S. Application Data

(60) Provisional application No. 62/431,911, filed on Dec. 9, 2016, provisional application No. 62/440,438, filed on Dec. 30, 2016.

(51) Int. Cl.
| | |
|---|---|
| *A61M 25/06* | (2006.01) |
| *A61M 25/01* | (2006.01) |
| *A61M 25/00* | (2006.01) |

(52) U.S. Cl.
CPC .... *A61M 25/0662* (2013.01); *A61M 25/0023* (2013.01); *A61M 25/0045* (2013.01);
(Continued)

(58) Field of Classification Search
CPC .......... A61M 25/0662; A61M 25/0023; A61M 25/0045; A61M 25/0113;
(Continued)

(56) References Cited

U.S. PATENT DOCUMENTS

| | | |
|---|---|---|
| 4,000,739 A | 1/1977 | Stevens |
| 4,289,128 A | 9/1981 | Rusch |

(Continued)

FOREIGN PATENT DOCUMENTS

| | | |
|---|---|---|
| CA | 2008784 C | 7/2002 |
| DE | 69928825 | 7/2006 |

(Continued)

OTHER PUBLICATIONS

Vascular Solutions, Inc. "GuideLiner V3 catheter: Guide Extension Catheter with Half-Pipe Technology" [Brochure], Dec. 2013, Minneapolis, MN.

(Continued)

*Primary Examiner* — Scott J Medway
*Assistant Examiner* — Courtney B Fredrickson
(74) *Attorney, Agent, or Firm* — Gregory W. Smock; Robert B. Madden

(57) ABSTRACT

Guide extension catheters and related methods are disclosed. A guide extension catheter can comprise an elongate tube member and a lumenless push member. The push member can be eccentrically coupled to the tube member for slidably positioning the tube member within and partially beyond a distal end of a guide catheter. At least a proximal end portion of the push member can include a cross-section defined by an arcuate first surface and an opposing second surface. The first surface can engage an inner wall surface of the guide catheter along an arc length, and the second surface can be spaced furthest from the first surface at its center point. The first surface can have the same or substantially the same radius of curvature as the guide catheter's inner wall surface, and the second surface can be flat or substantially flat. This configuration of the push member can provide an advantageous blend of stiffness and flexibility, as well as space conservation through the guide catheter.

20 Claims, 7 Drawing Sheets

(52) U.S. Cl.
CPC .... *A61M 25/0052* (2013.01); *A61M 25/0068* (2013.01); *A61M 25/0102* (2013.01); *A61M 25/0113* (2013.01); *A61M 2025/0047* (2013.01); *A61M 2025/0175* (2013.01)

(58) Field of Classification Search
CPC .. A61M 2025/0113; A61M 2025/0047; A61M 2025/0175
See application file for complete search history.

(56) References Cited

U.S. PATENT DOCUMENTS

| | | |
|---|---|---|
| 4,723,936 A | 2/1988 | Buchbinder et al. |
| 4,762,129 A | 8/1988 | Bonzel |
| 4,813,930 A | 3/1989 | Elliott |
| 4,832,028 A | 5/1989 | Patel |
| 4,838,268 A | 6/1989 | Keith et al. |
| 4,838,269 A | 6/1989 | Robinson et al. |
| 4,909,252 A | 3/1990 | Goldberger |
| 4,921,483 A | 5/1990 | Wijay et al. |
| 4,932,413 A | 6/1990 | Shockey et al. |
| 4,943,278 A | 7/1990 | Euteneuer et al. |
| 4,946,440 A | 8/1990 | Hall |
| 4,994,745 A | 2/1991 | Mizuta |
| 5,002,531 A | 3/1991 | Bonzel |
| 5,040,548 A | 8/1991 | Yock |
| 5,061,273 A | 10/1991 | Yock |
| 5,074,845 A | 12/1991 | Miraki et al. |
| 5,098,412 A | 3/1992 | Shiu |
| 5,102,403 A | 4/1992 | Alt |
| 5,120,323 A | 6/1992 | Shockey et al. |
| 5,122,125 A | 6/1992 | Deuss |
| 5,156,594 A | 10/1992 | Keith |
| 5,232,445 A | 8/1993 | Bonzel |
| 5,234,416 A | 8/1993 | Macaulay et al. |
| 5,257,974 A | 11/1993 | Cox |
| 5,267,958 A | 12/1993 | Buchbinder et al. |
| 5,290,247 A | 3/1994 | Crittenden |
| 5,328,472 A | 7/1994 | Steinke et al. |
| 5,350,395 A | 9/1994 | Yock |
| 5,368,567 A | 11/1994 | Lee |
| 5,383,853 A | 1/1995 | Jung et al. |
| 5,413,560 A | 5/1995 | Solar |
| 5,415,639 A | 5/1995 | VandenEinde et al. |
| 5,439,445 A | 8/1995 | Kontos |
| 5,441,489 A | 8/1995 | Utsumi et al. |
| 5,445,624 A | 8/1995 | Jimenez |
| 5,445,625 A | 8/1995 | Voda |
| 5,451,209 A | 9/1995 | Ainsworth et al. |
| 5,472,425 A | 12/1995 | Teirstein |
| 5,489,278 A | 2/1996 | Abrahamson |
| 5,527,292 A | 6/1996 | Adams et al. |
| 5,531,721 A | 7/1996 | Pepin et al. |
| 5,545,149 A | 8/1996 | Brin et al. |
| 5,549,553 A | 8/1996 | Ressemann et al. |
| 5,562,620 A | 10/1996 | Klein et al. |
| 5,567,203 A | 10/1996 | Euteneuer et al. |
| 5,571,087 A | 11/1996 | Ressemann et al. |
| 5,578,009 A | 11/1996 | Kraus et al. |
| 5,599,326 A | 2/1997 | Carter |
| 5,620,417 A | 4/1997 | Jang et al. |
| 5,649,909 A | 7/1997 | Cornelius |
| 5,658,263 A | 8/1997 | Dang et al. |
| 5,690,613 A | 11/1997 | Verbeek |
| 5,704,926 A | 1/1998 | Sutton |
| 5,720,300 A | 2/1998 | Fagan et al. |
| 5,720,724 A | 2/1998 | Ressemann et al. |
| 5,743,876 A | 4/1998 | Swanson |
| 5,772,642 A | 6/1998 | Ciamacco et al. |
| 5,776,141 A | 7/1998 | Klein et al. |
| 5,785,685 A | 7/1998 | Kugler et al. |
| 5,792,124 A | 8/1998 | Horrigan et al. |
| 5,843,022 A | 12/1998 | Willard et al. |
| 5,860,963 A | 1/1999 | Azam et al. |
| 5,891,056 A | 4/1999 | Ramzipoor |
| 5,902,290 A | 5/1999 | Peacock et al. |
| 5,911,715 A | 6/1999 | Berg et al. |
| 5,961,510 A | 10/1999 | Fugoso et al. |
| 5,980,486 A | 11/1999 | Enger |
| 6,042,578 A | 3/2000 | Dinh et al. |
| 6,071,273 A | 6/2000 | Euteneuer et al. |
| 6,159,195 A | 12/2000 | Ha et al. |
| 6,190,358 B1 | 2/2001 | Fitzmaurice et al. |
| 6,193,686 B1 | 2/2001 | Estrada et al. |
| 6,199,262 B1 | 3/2001 | Martin |
| 6,270,465 B1 | 8/2001 | Keith et al. |
| 6,299,628 B1 | 10/2001 | Harrison et al. |
| 6,338,725 B1 | 1/2002 | Hermann et al. |
| 6,398,773 B1 | 6/2002 | Bagaoisan et al. |
| 6,409,863 B1 | 6/2002 | Williams et al. |
| 6,443,912 B1 | 9/2002 | Mazzola et al. |
| 6,475,195 B1 | 11/2002 | Voda |
| 6,488,655 B1 | 12/2002 | Wantink et al. |
| 6,503,223 B1 | 1/2003 | Sekido et al. |
| 6,503,353 B1 | 1/2003 | Peterson et al. |
| 6,548,010 B1 | 4/2003 | Stivland et al. |
| 6,575,958 B1 | 6/2003 | Happ et al. |
| 6,591,472 B1 | 7/2003 | Noone et al. |
| 6,595,952 B2 | 7/2003 | Forsberg |
| 6,610,068 B1 | 8/2003 | Yang |
| 6,620,149 B1 | 9/2003 | Lenz et al. |
| 6,635,029 B1 | 10/2003 | Venturelli |
| 6,638,268 B2 | 10/2003 | Niazi |
| 6,648,874 B2 | 11/2003 | Parisi et al. |
| 6,689,144 B2 | 2/2004 | Gerberding |
| 6,706,018 B2 | 3/2004 | Westlund et al. |
| 6,733,487 B2 | 5/2004 | Keith et al. |
| 6,755,812 B2 | 6/2004 | Peterson et al. |
| 6,860,876 B2 | 3/2005 | Chen |
| 6,997,908 B2 | 2/2006 | Carrillo, Jr. et al. |
| 7,169,162 B2 | 1/2007 | Garakani |
| 7,232,452 B2 | 6/2007 | Adams et al. |
| 7,294,124 B2 | 11/2007 | Eidenschink |
| 7,374,560 B2 | 5/2008 | Ressemann et al. |
| 7,422,579 B2 | 9/2008 | Wahr et al. |
| 7,544,201 B2 | 6/2009 | Pepper |
| 7,604,612 B2 | 10/2009 | Ressemann et al. |
| 7,697,996 B2 | 4/2010 | Manning et al. |
| 7,717,899 B2 | 5/2010 | Bowe et al. |
| 7,736,355 B2 | 6/2010 | Itou et al. |
| 7,762,984 B2 | 7/2010 | Kumoyama et al. |
| 7,763,012 B2 | 7/2010 | Petrick et al. |
| 7,959,603 B2 | 6/2011 | Wahr et al. |
| 8,048,032 B2 | 11/2011 | Root et al. |
| 8,142,413 B2 | 3/2012 | Root et al. |
| 8,292,850 B2 | 10/2012 | Root et al. |
| 8,814,890 B2 | 8/2014 | Miyata et al. |
| RE45,380 E | 2/2015 | Root et al. |
| 8,996,095 B2 * | 3/2015 | Anderson ......... A61M 25/0105 600/434 |
| 9,144,662 B2 * | 9/2015 | Di Caprio ......... A61M 25/0068 |
| RE45,760 E | 10/2015 | Root et al. |
| RE45,776 E | 10/2015 | Root et al. |
| 9,352,123 B2 * | 5/2016 | Zhou ................ A61M 25/0069 |
| RE46,116 E | 8/2016 | Root et al. |
| 9,486,611 B2 * | 11/2016 | Petersen ............... A61M 25/01 |
| 10,173,029 B2 | 1/2019 | Webster et al. |
| RE47,379 E | 5/2019 | Root et al. |
| 2001/0016712 A1 | 8/2001 | Hamilton |
| 2002/0165598 A1 | 11/2002 | Wahr et al. |
| 2003/0195546 A1 | 10/2003 | Solar et al. |
| 2003/0233117 A1 | 12/2003 | Adams et al. |
| 2004/0010280 A1 | 1/2004 | Adams et al. |
| 2004/0127927 A1 | 7/2004 | Adams |
| 2004/0236215 A1 | 11/2004 | Mihara et al. |
| 2005/0004523 A1 | 1/2005 | Osborne et al. |
| 2005/0015073 A1 | 1/2005 | Kataishi et al. |
| 2005/0182437 A1 | 8/2005 | Bonnette et al. |
| 2006/0247661 A1 | 11/2006 | Richards et al. |
| 2007/0260219 A1 | 11/2007 | Root et al. |
| 2008/0243171 A1 | 10/2008 | Ressemann et al. |
| 2009/0005755 A1 | 1/2009 | Keith et al. |
| 2009/0264865 A1 | 10/2009 | Kawai |
| 2013/0072904 A1 | 3/2013 | Musbach et al. |

(56) References Cited

U.S. PATENT DOCUMENTS

| | | | |
|---|---|---|---|
| 2013/0116701 A1 | 5/2013 | Wang et al. | |
| 2013/0197483 A1 | 8/2013 | Anderson et al. | |
| 2014/0018773 A1 | 1/2014 | Wang et al. | |
| 2014/0039461 A1 | 2/2014 | Anderson et al. | |
| 2014/0081243 A1 | 3/2014 | Zhou et al. | |
| 2014/0142506 A1 | 5/2014 | Prindle et al. | |
| 2014/0276618 A1 | 9/2014 | Di Caprio et al. | |
| 2015/0151090 A1* | 6/2015 | Sutton .............. | A61M 25/0662 600/585 |
| 2016/0346515 A1 | 12/2016 | Buller et al. | |

FOREIGN PATENT DOCUMENTS

| | | |
|---|---|---|
| EP | 0313558 B1 | 1/1991 |
| EP | 0380873 B1 | 5/1994 |
| EP | 0365993 B1 | 12/1994 |
| EP | 0881921 A1 | 12/1998 |
| EP | 1084728 A1 | 3/2001 |
| EP | 099260 B1 | 9/2007 |
| JP | 2004275435 A | 10/2004 |
| WO | 1984003633 A1 | 9/1984 |
| WO | 1997037713 A1 | 10/1997 |
| WO | 2000024451 A9 | 11/2000 |
| WO | 2016191415 A1 | 12/2016 |
| WO | 2017019900 A1 | 2/2017 |

OTHER PUBLICATIONS

PCT International Search Report dated Apr. 29, 2019, in PCT application No. PCT/US2019/016234.

Bertrand, Michel E. "The Evolution of Cardiac Catheterization and Interventional Cardiology," European Society of cardiology, 2006, 10 pages.

Bonzel, T. et al. "The Sliding Rail System (Monorail): Description of a New Technique for Intravascular Instrumentation and its Application to Coronary Angioplasty," Z. Kardiol. 76, Supp. 6 (1987), pp. 119-122.

Iqbal et al. "Coronary stents: historical development, current status and future directions," British Medical Bulletin, 2013, 106: 193-211.

Topol, Eric J. "Textbook of Interventional Cardiology," Saunders Elseveir, 5th Edition, 2008, p. 277-280.

Tully, Shawn. "Blood Feud This little piece of metal is worth $4.5 billion this year, generates more profits than a blockbuster drug, and has sparked one of the weirdest corporate battles ever. It could also save your life." CNN Money, May 31, 2004, 5 pages. Retrieved Jan. 14, 2019 on the Internet: .

Takahashi, Saeko. "New Method to Increase a Backup Support of a 6 French Guiding Coronary Catheter," Catheterization and Cardiovascular Interventions 63:452-456 (2004), 5 pages, published online in Wiley InterScience (www.interscience.wiley.com).

EP search report dated Apr. 16, 2018, in European Application No. 17193571.1 filed Sep. 27, 2017.

PCT International Preliminary Report on Patentability dated Dec. 16, 2019, in PCT application No. PCT/US2019/016235.

* cited by examiner

GUIDE EXTENSION CATHETER

CLAIM OF PRIORITY

This non-provisional patent document claims the benefit of priority under 35 U.S.C. § 119(e) to Brenizer et al., U.S. Provisional Patent Application Ser. No. 62/431,911, entitled "GUIDE EXTENSION CATHETER" and filed on Dec. 9, 2016, and to Brenizer et al., U.S. Provisional Patent Application Ser. No. 62/440,438, entitled "GUIDE EXTENSION CATHETER" and filed on Dec. 30, 2016, each of which is herein incorporated by reference in its entirety.

TECHNICAL FIELD

This patent document relates to medical devices. More particularly, but not by way of limitation, the patent document relates to guide extension catheters for use with guide catheters.

BACKGROUND

A guide catheter can back-out and withdraw from a vessel's ostium or branch when an interventional device, such as a guidewire, balloon catheter, stent or stent catheter, is passed through it and advanced beyond the guide catheter's distal end. This backing out of the guide catheter can cause the operating physician to lose the ability to further distally advance the interventional device.

OVERVIEW

The present inventors recognize that there is a need to provide increased back-up support to interventional devices and guide catheters during interventional procedures. A guide extension catheter can be used in conjunction with a guide catheter to access discrete regions of coronary or peripheral vasculature and to facilitate accurate placement of interventional devices without guide catheter back-out from a vessel ostium or branch of interest. The guide extension catheter can also provide a means for delivering drugs or providing negative pressure to and from a treatment site. The present inventors further recognize that the interventional art would benefit from the availability of a guide extension catheter that can be effectively and efficiently urged through a guide catheter and have its distal end deep-seated into the vessel portion of interest without kinking or bending improperly, without reducing the device delivery area through the guide catheter, and without becoming entangled with a guidewire.

Guide extension catheters and related methods are disclosed in this patent document. A guide extension catheter can comprise an elongate tube member and a lumenless push member. The push member can be eccentrically coupled to the tube member for slidably positioning the tube member within and partially beyond a distal end of a guide catheter and a vessel ostium of interest. At least a proximal end portion of the push member can include a cross-section defined by an arcuate first surface and an opposing second surface. The first surface can engage an inner wall surface of the guide catheter along an arc length, and the second surface can be spaced furthest from the first surface at its center point. The first surface can have the same or substantially the same radius of curvature as the guide catheter's inner wall surface, and the second surface can be flat or substantially flat, for example. This configuration of the push member can provide an advantageous blend of stiffness, flexibility and space conservation through the guide catheter. The push member can include one or more means along its length to urge the push member to one side of the guide catheter's inner wall surface, thereby providing a clear path through the guide catheter and into the guide extension catheter for an interventional device.

These and other embodiments and features of the present guide extension catheters and related methods will be set forth, at least in part, in the following Detailed Description. This Overview is intended to provide non-limiting embodiments of the present subject matter—it is not intended to provide an exclusive or exhaustive explanation of the disclosed embodiments. The Detailed Description below is included to provide further information about the present guide extension catheters and methods.

BRIEF DESCRIPTION OF THE DRAWINGS

In the drawings, like numerals can be used to describe similar features and components throughout the several views. The drawings illustrate generally, by way of example, but not by way of limitation, various embodiments discussed in this patent document.

The drawings are not necessarily to scale. Certain features and components may be shown exaggerated in scale or in schematic form, and some details may not be shown in the interest of clarity and conciseness.

DETAILED DESCRIPTION

This patent document discloses guide extension catheters to be placed within guide catheters for providing support and guidance in a vessel when percutaneously advancing interventional devices, such as guidewires, balloon catheters, stents or stent catheters. A guide extension catheter is configured to be passed through a main lumen of a guide catheter so that its distal end portion can be extended past a distal end of the guide catheter and into the desired vessel while its intermediate portions remain within the guide catheter. The guide extension catheter improves the ability of the guide catheter to remain seated in the desired vessel's ostium or branch during an interventional procedure.

It is believed that the present guide extension catheters will find great utility by interventional cardiologists performing percutaneous transluminal coronary interventions.

Although the remainder of this patent document generally discusses and illustrates such uses, it should be understood that the guide extension catheters can also be used for treating other non-coronary diseased vessels or other hollow structures (e.g., biliary tract, ureter, etc.) throughout a patient's body where interventional devices are or can be employed.

Figure 1:
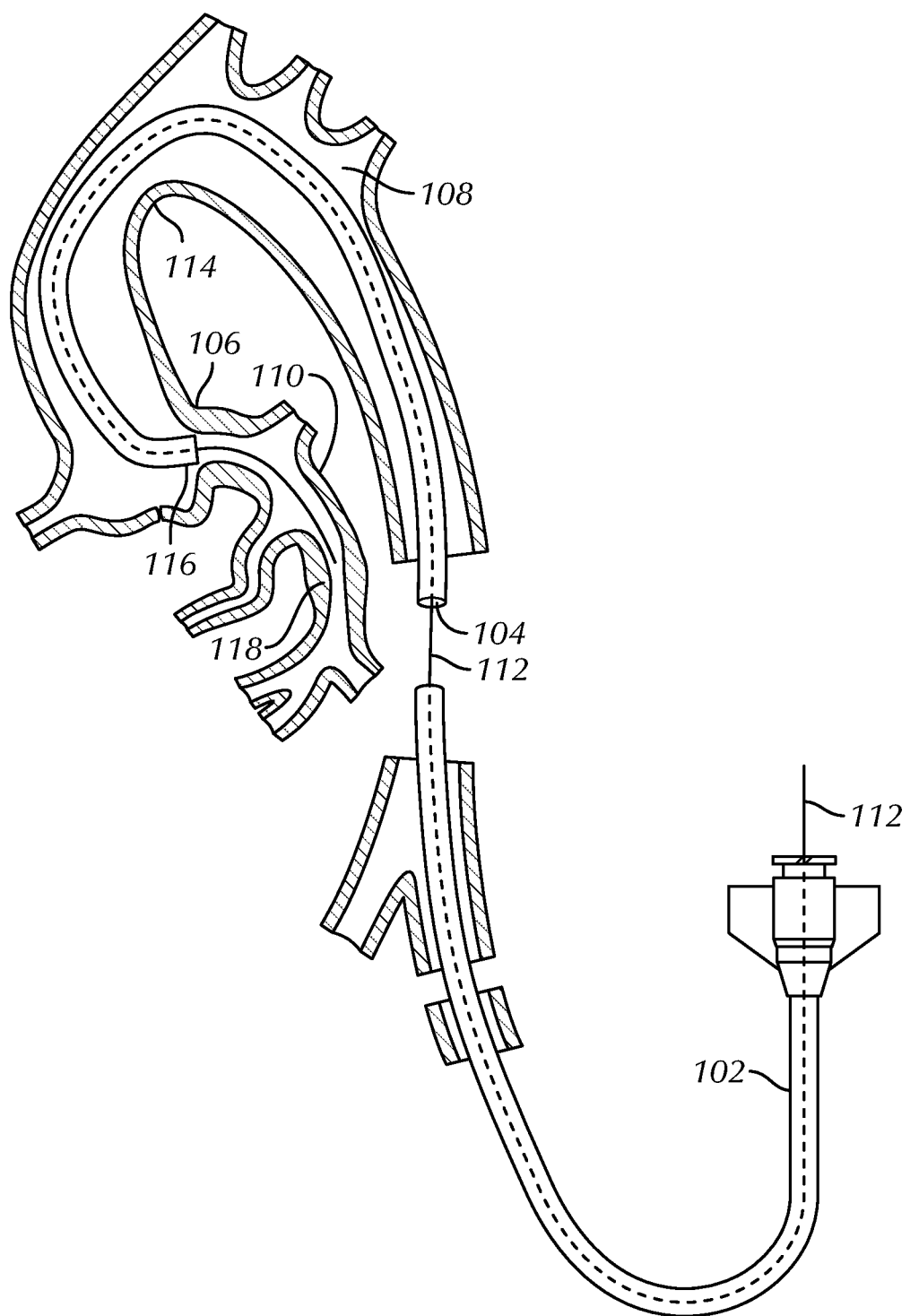
FIG. 1 illustrates a plan view of a guide catheter advanced through an aorta to an ostium of a coronary vessel.

Minimally-invasive cardiac interventions are utilized throughout the world and include the use of a guidewire 112 and a guide catheter 102, as illustrated in FIG. 1. The guidewire 112 is an elongate, small-diameter member designed to navigate vessels to reach a diseased site or vessel segment of interest. Guidewires come in two basic configurations: solid steel or nitinol core wires and solid core wire wrapped in a smaller wire coil or braid. The guide catheter 102 is an elongate tube member defining a main lumen 104 along its length. The guide catheter 102 can be formed of polyurethane, for example, and can be shaped to facilitate its advancement to a coronary ostium 106 (or other region of interest within a patient's body). In the embodiment of FIG. 1, a 4 F, 5 F, 6 F, 7 F or 8 F guide catheter 102, where F is an abbreviation for the French catheter scale (a unit to measure catheter diameter (1 F=¼ mm)), can be inserted at a femoral or radial artery and advanced through an aorta 108 to a position adjacent to the ostium 106 of a coronary artery 110.

In a typical procedure, the guidewire 112 is advanced through the arch 114 of the aorta 108 to the ostium 106. The guide catheter 102 is then passed over the guidewire 112 until its distal end 116 is seated near the ostium 106. The diameter and rigidity of the guide catheter's distal end 116 oftentimes does not permit the device to be advanced beyond the ostium 106 and into the coronary artery 110.

Maintaining the position of the guide catheter's distal end 116 at the ostium 106 can facilitate the guidewire 112 or other interventional device successfully reaching the diseased site (e.g., a stenotic lesion 118) through its further distal advancement. With the guide catheter 102 in position, force can be applied to the guidewire's proximal end to push the guidewire 112 to and beyond the lesion 118, and a treating catheter (optionally including a balloon or stent) can be passed over the guidewire 112 to treat the site. The application of force to the guidewire 112 or the treating catheter can sometimes cause the guide catheter 102 to dislodge from the ostium 106 of the coronary artery 110, and, in such instances, the guidewire or treating catheter must be further distally advanced independently of the guide catheter's alignment and support to reach the lesion 118. This can occur in the case of a tough stenotic lesion 118 or tortuous anatomy, where it is difficult to pass the guidewire 112 or the treating catheter to and beyond the lesion. A heart's intrinsic beat can also cause the guide catheter's distal end 116 to lose its positioning or otherwise be shifted so that it no longer is positioned to align and support the guidewire 112 or the treating catheter into the portion of the coronary artery 110 including the lesion 118.

Figure 2:
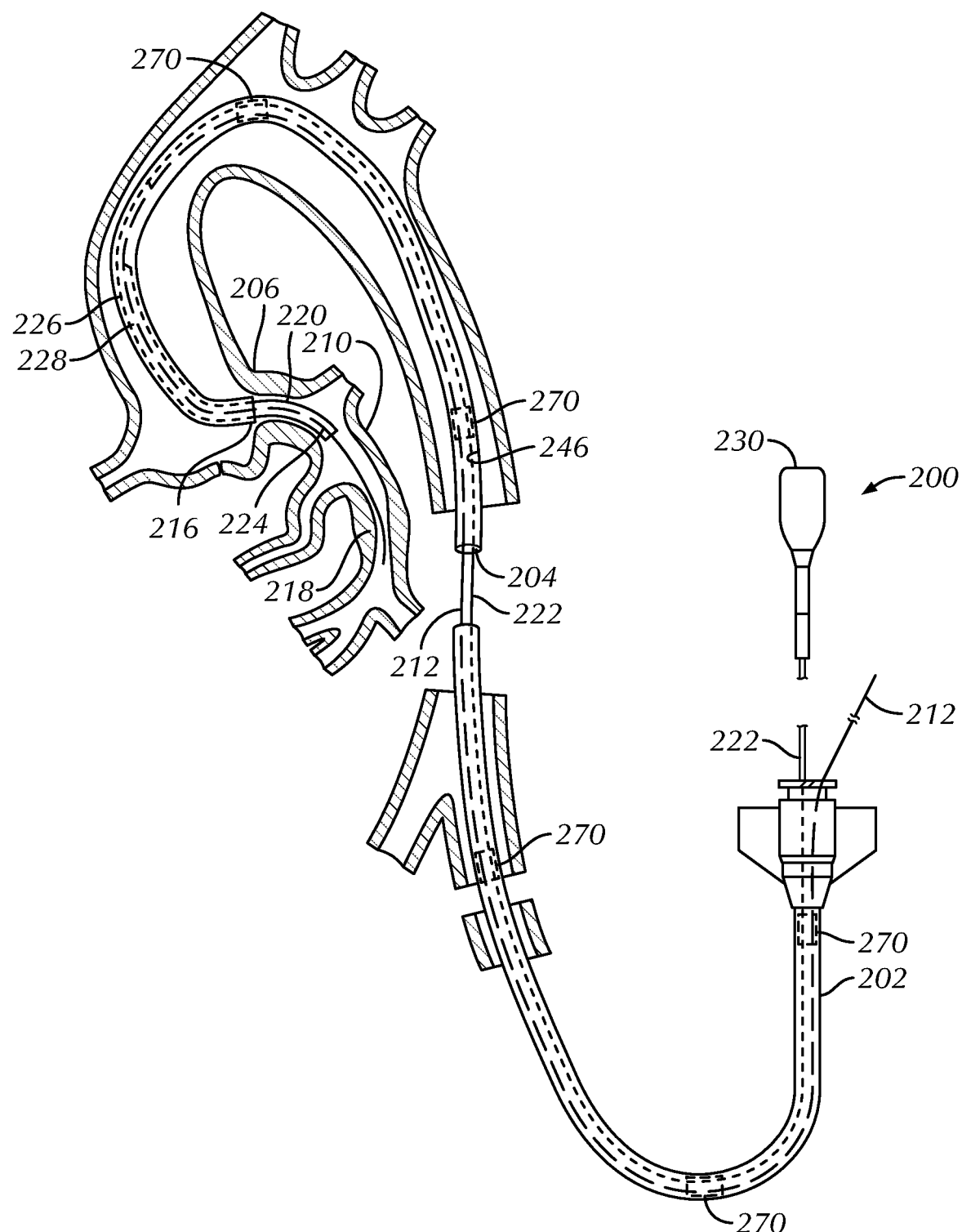
FIG. 2 illustrates a plan view of a guide extension catheter, as constructed in accordance with at least one embodiment, used in conjunction with a guide catheter for the delivery of an interventional device into an occluded vessel for treatment.

As illustrated in FIG. 2, the present guide extension catheter 200 can improve access to a coronary artery 210 and a stenotic lesion 218. The guide extension catheter 200 can include a relatively flexible elongate tube member 220 and a push member 222 having a collective length that is greater than a length of a guide catheter 202 (e.g., 130 cm-175 cm). An outer diameter of the tube member 220 can be sized to permit insertion of its distal end portion 224 into a coronary artery or its branches containing the lesion 218, thereby providing alignment and support for an interventional device (e.g., a treating catheter) beyond the distal end 216 of the guide catheter 202 to the lesion and beyond. The extension of the tube member 220 into the smaller-sized artery or branch also serves to maintain the position of the guide catheter 202 at an artery's ostium 206 during operation.

The operating physician can advance the distal end portion 224 of the tube member 220 over a guidewire 212 and through and beyond the guide catheter's distal end 216 into the coronary artery 210. A proximal end portion 226 of the tube member 220 can remain within the guide catheter 202. The physician can then deliver the treating catheter over the guidewire 212, through a main lumen 204 of the guide catheter 202, and through a lumen 228 of the tube member 220 until the working portion of the treating catheter is located beyond the distal end portion 224 of the tube member. The operating physician can then treat the lesion 218 using standard techniques with added back-up support on the guide catheter 202, thereby providing an extra ability to push and advance the treating catheter.

In general, the lumen 228, and hence the tube member 220, can be sized and shaped to pass one or more interventional devices such as the guidewire and the treating catheter therethrough. The cross-sectional shape of the lumen 228 can be similar to the cross-sectional shape of the guide catheter's main lumen 204. The outer diameter of the tube member 220 can assume maximum cross-sectional dimensions that allow the tube member 220 to coaxially slide into and through the guide catheter 202. In other embodiments, the outer cross-sectional dimensions of the tube member 220 can be less than the allowable maximum. For example, in an 8 F guide catheter, the tube member 220 can have a 7 F, 6 F, 5 F, 4 F or lesser diameter. In some embodiments, a diameter of the lumen 228 of the tube member 220 is not more than one French size smaller than a diameter of the lumen 204 of the guide catheter 202. The length of the tube member 220 can be substantially less than the length of the guide catheter 202; however, the tube member 220 can be designed with any length according to a desired application, such as about 6 cm-45 cm.

The push member 222 can be attached at least to the proximal end portion 226 of the tube member 220 and can extend proximally from this attachment to a handle member 230 accessible to an operating physician outside of a patient's body. The handle member 230 and the push member 222 can allow the physician to position the tube member 220 between a first position, entirely within the guide catheter 202, and the illustrated second position, in which the tube member's distal end 224 extends beyond that of the guide catheter 202 and into the coronary artery 210. The push member 222 can include one or more tubular bands 270 or other means along its length to urge the member to one side of the guide catheter's inner wall surface 246, thereby providing a clear path through the guide catheter and into the guide extension catheter 202 for the guidewire 212 and treating catheter. This clear path can avoid or reduce the guidewire 212 becoming entangled with (e.g., wrapped around) the push member 222 during use of the guide extension catheter 202.

Figure 3:
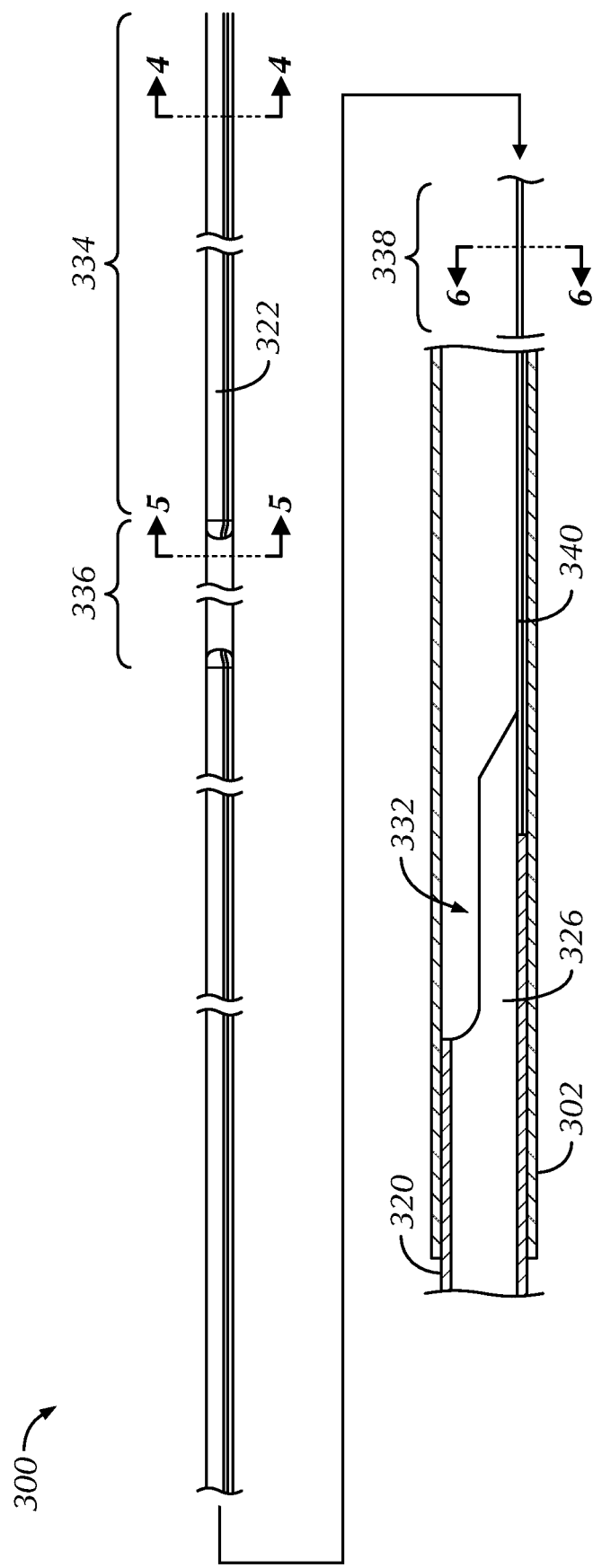
FIG. 3 illustrates a side view of a guide extension catheter, as constructed in accordance with at least one embodiment, partially within a sectioned guide catheter.

FIG. 3 illustrates a side view of a guide extension catheter 300 partially positioned within a guide catheter 302. This side view illustrates in greater detail the two primary components of the guide extension catheter 300—a relatively flexible elongate tube member 320 and a push member 322. In certain embodiments, the push member 322 can include a plurality of segments or portions having different stiffness and flexibility profiles to provide the guide extension catheter 300 with a desired combination of pushing force and vessel placement capabilities. In one embodiment, as shown in cross-sections at FIGS. 4-6, the push member 322 can include three segments 334, 336, 338 having different stiffness and flexibility profiles: relative high stiffness and low flexibility at a proximal end portion of the push member, relative medium stiffness and flexibility in an intermediate portion of the push member, and relative low stiffness and high flexibility at a distal end portion of the push member. In some embodiments, the length of the first segment 334 makes up between 50% to 90% of the entire length of the guide extension catheter 300, the length of the third segment 338 makes up between 2% to 10% of the catheter's length, and the remaining length can be attributed to the second segment 336. More or less segments of differing stiffness and flexibility profiles can also be used and accomplished through variation of one or more of materials, geometrical shapes or geometrical sizes of the push member 322.

The push member 322 can be an elongated solid wire of constant or varying dimensions and can made of a polymeric or metallic material, such as high tensile stainless steel (e.g., 304V, 304L or 316LV), mild steel, nickel-titanium alloys, nickel-chromium-molybdenum alloys, nickel-copper alloys, nickel-tungsten alloys or tungsten alloys. The push member 322 can be coated with a hydrophilic, silicone or other friction-reducing material. A handle member (FIG. 2) at the push member's proximal end can be formed of a polycarbonate material, for example.

The tube member 320 can be formed from an inner polymer layer, an outer polymer layer, and a reinforcement member (e.g., braid or coil) disposed between the polymer layers. The inner polymer layer can be composed of, or coated with, silicone, polytetrafluoroethylene (PTFE) or another lubricious material to provide a slippery surface for received interventional devices. The outer polymer layer can include one or more flexible materials, such as polyurethane, polyethylene or polyolefin of sequentially diminishing durometers along the tube member's length, and it can be coated with a friction-reducing material (e.g., a hydrophilic material) to facilitate insertion and trackability through vasculature and a guide catheter. The reinforcing braid or coil can be formed of stainless steel or a platinum alloy, for example, and can extend between the polymer layers along at least a portion of the tube member's length.

A proximal end portion 326 of the tube member 320 can be eccentrically coupled to a distal end portion 340 of the push member 322 at its periphery or circumference and can provide a smooth transition between the members. The arrangement or configuration of this coupling can vary. For example, the tube member 320 can have an opening formed in its peripheral wall and the push member 322 can be disposed within the opening. Inserting the push member 322 into the opening can result in a mechanical coupling between the members and additional or alternative bonds (e.g., adhesive bonds, thermal bonds, welds, brazes, etc.) can be utilized. The distal end portion 340 of the push member 322 can be flattened to provide a larger surface area to secure to the tube member 320. Coupling mechanisms facilitated by a third component 332 (e.g., a metal or polymer skived (slanted) collar or concave track) bonded between or integrated with the proximal end portion 326 of the tube member 320 or the distal end portion 340 of the push member 322 are also contemplated. Metallic or polymeric structures forming the third component 332 can become less stiff and more flexible in a proximal-to-distal direction to provide a gradual flexibility transition between the more rigid push member 322 and the more flexible tube member 320.

Markers on the push member 322 or the tube member 320 can allow an operating physician to identify positioning of the guide extension catheter's components relative to patient anatomy, the guide catheter 302, and any international devices used during a procedure. For example, one or more depth markers can be printed on an outer surface of the push member 322 and can be positioned at predetermined lengths relative to a distal end of the tube member 320. One or more radiopaque marker bands can be positioned on the tube member 320. The marker bands can be composed of tungsten, platinum or an alloy thereof and can have a metallic band structure. Alternatively, for space conservation reasons, the marker bands can be formed by impregnating portions of the tube member 320 with a radiopaque filler material, such as such as barium sulfate, bismuth trioxide, bismuth carbonate, powdered tungsten, powdered tantalum or the like. A first marker band can be positioned slightly distal to a fully-round entrance of the tube member 320 and a second marker band can be positioned near the tube member's distal end, for example.

Figure 4:
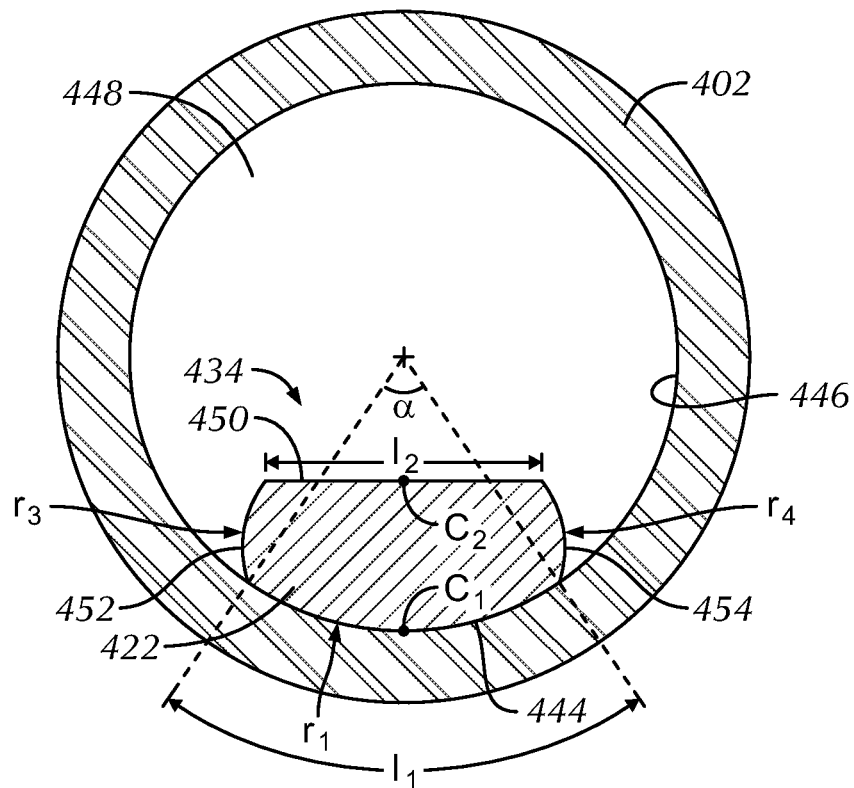
FIGS. 4-6 illustrate cross-sectional views along the length of a guide extension catheter's push member, as constructed in accordance with at least one embodiment, within a guide catheter.

FIG. 4 illustrates a cross-sectional view of a proximal end portion 434 of a push member 422, such as along line 4-4 of FIG. 3, within a guide catheter 402. The cross-section can be defined by an arcuate first surface 444 configured to engage an inner wall surface 446 of the guide catheter 402 along an arc length ($l_1$) (e.g., 0.030 in) defined by a guide catheter central angle ($\alpha$) of at least 20 degrees, at least 30 degrees, at least 40 degrees, at least 50 degrees or at least 60 degrees, with greater arc lengths ($l_1$) associated with greater central angles ($\alpha$). The arcuate or curved shape of the first surface 444 follows the inner wall surface 446 of the guide catheter 402 providing smooth relative movements between the guide extension catheter and the guide catheter. The arcuate shape of the first surface 444 can also help to maximize axial or column strength of the push member 422 for force transfer from an operating physician to the rest of the guide extension catheter without reducing the effective delivery area 448 within the guide catheter 402 through which an interventional device can be advanced. In an embodiment, the first surface 444 can have the same or substantially the same radius of curvature ($r_1$) as the guide catheter's inner wall surface 446, such as a radius of curvature of about 0.035 in.

A second surface 450 of the proximal end portion's cross-section, which is positioned opposite the first surface 444, can be flat or substantially flat and have a length ($l_2$) (e.g., 0.026 in) that is less than the arc length ($l_1$) of the first surface. The second surface 450 can be spaced furthest from the first surface at its center point ($c_2$). In an embodiment, the center point ($c_2$) of the second surface 450 is at least 0.010 in (e.g., 0.014 in) from a center portion ($c_1$) of the first surface 444. In an embodiment, a distance between center points ($c_1$, $c_2$) of the first and second surfaces 444, 450 can be between 40-60% of the arc length ($l_1$) of the first surface.

The cross-section at the proximal end portion of the push member 422 can be further defined by third and four arcuate surfaces 452, 454 that connect the first and second surfaces 444, 450. The third and four surfaces 452, 454 can have a radius of curvature ($r_{3,4}$) less than the radius of curvature ($r_1$) of the first surface 444. In an embodiment, the radius of curvature ($r_1$) of the first surface (e.g., 0.035 in) is at least three times greater than the radius of curvature ($r_{3,4}$) of the third and fourth surfaces (e.g., 0.010 in).

It has been found that this cross-sectional configuration of the proximal end portion 434 of the push member 422 can be desirable for a number of reasons. The configuration, which resembles a bread loaf in its cross-sectional shape, can increase the push force capability and the torque control of the push member 422 as compared to a flat rectangular ribbon. Accordingly, greater axial and rotational force applied by the operating physician to the push member's proximal end portion 434 can be transmitted to the tube member. In this manner, the tube member can more reliably be urged through obstructions or into a tortuous portion of the patient's vasculature.

Figure 5:
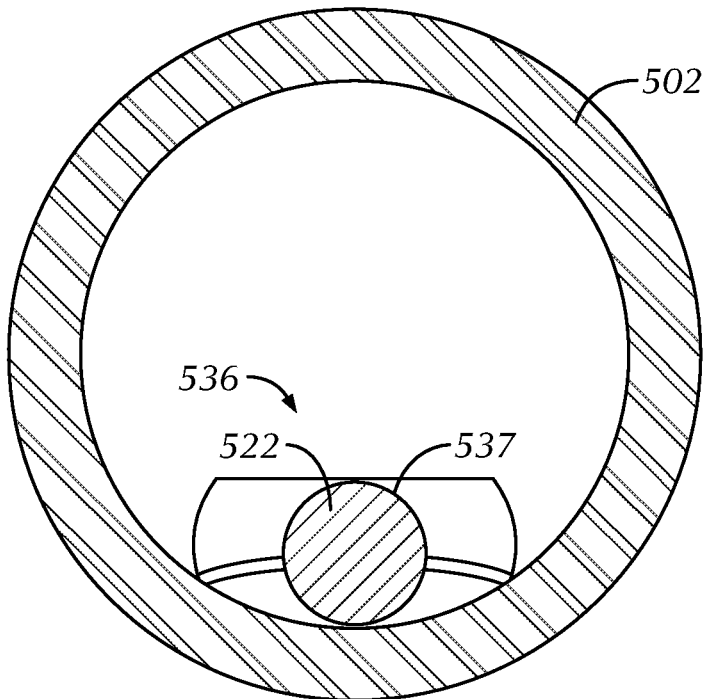

FIG. 5 illustrates a cross-sectional view of an intermediate portion 536 of a push member 522, such as along line 5-5 of FIG. 3, within a guide catheter 502. As shown, the intermediate portion 536 can be circular or oval in cross-section and defined by a circumferential surface 537, which can reduce the tendency for a guidewire to become engaged with the push member 522 during use. In an embodiment, the circumferential surface 537 has a diameter of about 0.013 in.

Alternatively, the intermediate portion 536 can be rectangular in cross-section and defined by first, second, third and fourth flat surfaces, or can be bread loaf in cross-section and defined by three arcuate surfaces and one flat surface similar to the proximal end portion. In these alternative embodiments, a distance change between center points of the first and second surfaces at the push member's proximal end portion (FIG. 4) to center points of the first and second surfaces at the push member's intermediate portion is less than a distance change between center points of the third and fourth surfaces at the push member's proximal end portion to center points of the third and fourth surfaces at the push member's intermediate portion.

As yet another alternative, the intermediate portion 536 can have a cross-section defined by arcuate first and second surfaces. An arcuate first surface can have the same or substantially the same radius of curvature as the guide catheter's inner wall surface. An arcuate second surface can extend from a first end of the first surface to a second end of the first surface. Regardless of shape, the cross-section of the intermediate portion 536 of the push member can define an area less than an area of the cross-section of the proximal end portion (FIG. 4) of the push member 522.

Figure 6:
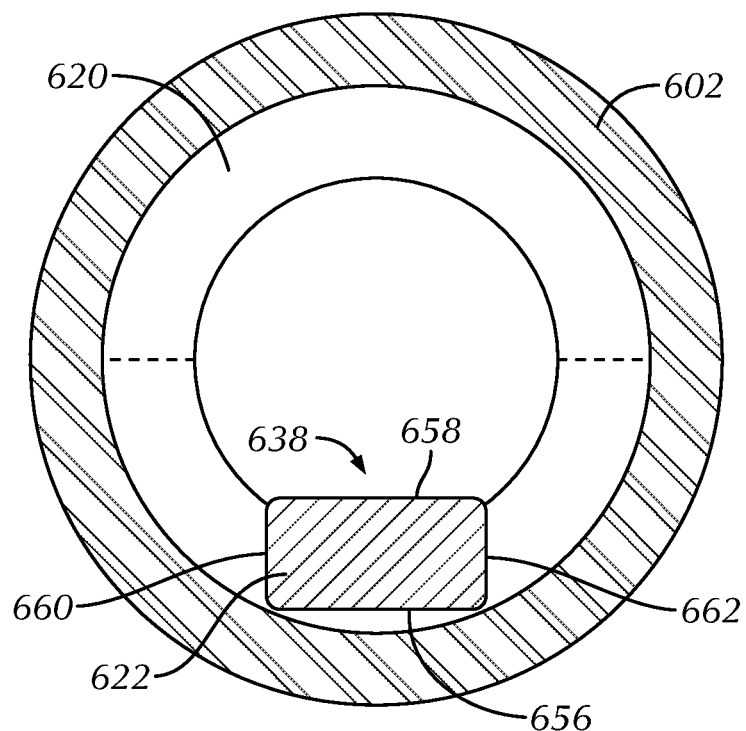

FIG. 6 illustrates a cross-sectional view of a distal end portion 638 of a push member 622, such as along line 6-6 of FIG. 3, within a guide catheter 602. The distal end portion 638 can be rectangular in cross-section and defined by first, second, third and fourth flat surfaces 656, 658, 660, 662. The cross-section of the distal end portion 638 can define an area less than an area of the cross-section of the proximal end (FIG. 4) and intermediate (FIG. 5) portions of the push member 622. In an embodiment, the first and second surfaces 656, 658 have a length of 0.020 in., and the third and fourth surfaces 660, 662 have a length of 0.010 in. The cross-section of the stiffer proximal end portion can gradually transition along the length of the push member 622 to the more flexible cross-section of the distal end portion 638, which can couple to a tube member 620. The flattened rectangular cross-section of the distal end portion 638 can provide sufficient attachment surface area to attach the push member 622 to the tube member 620. Alternatively, the distal end portion 638 can be bread loaf in cross-section and defined by three arcuate surfaces and one flat or substantially flat surface similar to the proximal end portion.

FIGS. 4-6 illustrate that the push member 422, 522, 622 of a guide extension catheter can be designed to be sufficiently small taking up relatively little space within the lumen of a guide catheter, while still being sufficiently sized and configured for exceptional pushability and kink resistance when advancing the extension catheter during an interventional procedure. Accordingly, use of the present guide extension catheters allows for an interventional device to be advanced through and beyond the guide catheter in order to reach a desired distal target location for intervention.

Figure 7:
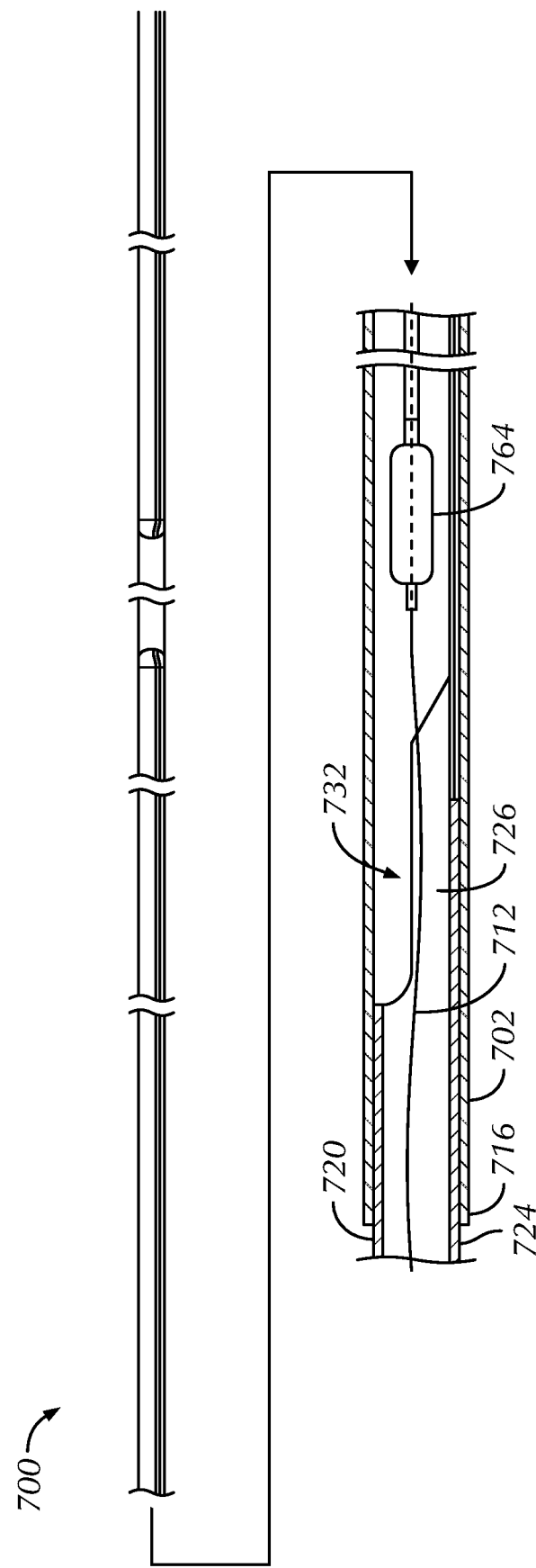
FIG. 7 illustrates a side view of a guide extension catheter, as constructed in accordance with at least one embodiment, and an interventional device partially within a sectioned guide catheter.

FIG. 7 illustrates a side view of a guide extension catheter 700 positioned within a guide catheter 702 and used in conjunction with a guidewire 712 and a treating catheter 764. With the guidewire 712 and the guide catheter 702 positioned as desired, a tube member 720 of the guide extension catheter 700 can be backloaded from its distal end portion 724 onto a proximal end of the guidewire 712 and advanced through a hemostasis valve coupled to the guide catheter 702. As shown, the tube member 720 of the guide extension catheter 700 can be advanced beyond a distal end 716 of the guide catheter 702 under fluoroscopy. When so arranged, portions of the tube member 720 can engage an ostium and extend within a portion of a coronary artery to help maintain the position of the guide catheter 702 as the treating catheter 764 is advanced.

Figure 8:
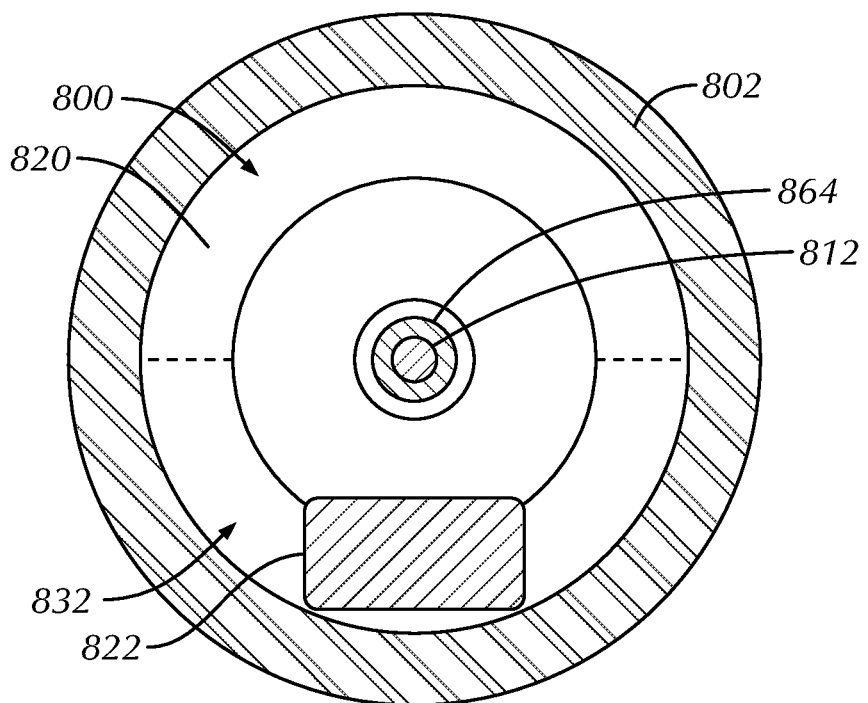
FIG. 8 illustrates a cross-sectional view of a guide extension catheter, as constructed in accordance with at least one embodiment, and an interventional device within a guide catheter.

FIG. 8 illustrates a cross-sectional view of a guide extension catheter 800, a guidewire 812 and a treating catheter 864 within a guide catheter 802, such as along line 8-8 of FIG. 7. It can be seen that use of the present eccentrically-positioned push member 822 to adjust a position of a tube member 820 of the guide extension catheter 800 can provide several advantages. As a first example, the relatively small dimensions of the push member 822 create low surface friction during its longitudinal movement within the guide catheter 802. Low frictional force allows ease in extending and retrieving the tube member 820. As another example, the small cross-sectional dimensions of the push member 822 do not significantly interfere with the delivery of the treating catheter 864 through the guide catheter 802.

Delivery of the treating catheter 764, 864 through the guide catheter 702, 802 and into the tube member 720, 820 can be facilitated by a concave track 732, 832 defining a partially cylindrical opening and having a length of about 1 cm to 18 cm. The concave track 732, 832 is accessible from a longitudinal side defined transverse to a longitudinal axis of the tube member 720, 820 and provides a larger area to receive an interventional device into the tube member than an area associated with an opening oriented perpendicular to the longitudinal axis of the tube member. Optionally, the concave track 732, 832 can be sized larger than the tube member 720, 820 (e.g., 7 F or 8 F outer diameter for the concave track and 6 F outer diameter for the tube member) to more effectively align and funnel the treating catheter 764, 864 across the coupling transition and into the tube member 720, 820. This larger size of the concave track 732, 832 can be accomplished by incorporating a nickel-titanium alloy, for example, which can expand post-implant to a size of the guide catheter's inner wall surface.

The concave track 732, 832 can be positioned between or integrated with the proximal end portion of the tube member 720, 820 or the distal end portion of the push member 722, 822. In an embodiment, a first segment of the concave track 732, 832 can have an arcuate cross-sectional shape extending for a length of at least 0.5 cm and radially extending 25% to 40% of a cross-sectional circumference of the guide catheter 702, 802 or the tube member 720, 820. A second segment of the concave track 732, 832 can have a hemicylindrical cross-sectional shape extending for a length of at least 0.5 cm and radially extending 40% to 70% of a cross-sectional circumference of the guide catheter 702, 802 or the tube member 720, 820.

In lieu of the concave track 732, 832, the proximal end portion 726 of the tube member 720, 820 can be partially (e.g., top half only) or completely radially flared to be larger in size than other portions of the tube member and coincide with the inner diameter of the guide catheter 702, 802. The close fit between the flared proximal end portion and the guide catheter 702, 802 can be used to align and funnel the treating catheter 764, 864, for example, from the guide catheter lumen into the tube member lumen, as well as direct fluid injected through the guide catheter into the tube member lumen. The flare can be accomplished by molding the tube member's 720, 820 proximal end portion or by incorporating a size- or shape-changing alloy (e.g., a nickel-titanium alloy) into the tube member's 720, 820 proximal end portion.

EXAMPLES

The above Detailed Description is intended to be illustrative and not restrictive. The above-described embodiments (or one or more features or components thereof) can be used in varying combinations with each other unless clearly stated to the contrary. Other embodiments can be used, such as by one of ordinary skill in the art upon reviewing the above Detailed Description. Also, various features or components have been grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment.

In Example 1, a guide extension catheter for use with a guide catheter can comprise an elongate tube member and a push member eccentrically coupled to the tube member. The tube member can define a lumen and have an outer diameter smaller than a lumen of the guide catheter. The push member can extend proximally from its point of coupling with the tube member for slidably positioning the tube member within and partially beyond a distal end of the guide catheter. At least a proximal end portion of the push member can include a cross-section defined by an arcuate first surface, which is configured to engage an inner wall surface of the guide catheter along an arc length defined by a guide catheter central angle of at least 20 degrees, and a second surface, which is opposite the first surface and has a center point at least 0.010 inches from a center point of the first surface.

In Example 2, the guide extension catheter of Example 1 can optionally be configured such that the first surface of the push member's proximal end portion has the same radius of curvature as the guide catheter's inner wall surface.

In Example 3, the guide extension catheter of Example 2 can optionally be configured such that the cross-section of the proximal end portion of the push member is further defined by third and four arcuate surfaces that connect the first and second surfaces. The third and four surfaces can have a radius of curvature less than the radius of curvature of the first surface.

In Example 4, the guide extension catheter of Example 3 can optionally be configured such that the radius of curvature of the first surface is at least three times greater than the radius of curvature of the third and fourth surfaces.

In Example 5, the guide extension catheter of any one or any combination of Examples 1-4 can optionally be configured such that the second surface is flat.

In Example 6, the guide extension catheter of any one or any combination of Examples 1-5 can optionally be configured such that the push member is solid.

In Example 7, the guide extension catheter of any one or any combination of Examples 1-6 can optionally be configured such that an intermediate or distal end portion of the push member includes a rectangular cross-section defining an area less than an area of the cross-section of the proximal end portion of the push member.

In Example 8, the guide extension catheter of any one or any combination of Examples 1-7 can optionally be configured such that an intermediate or distal end portion of the push member includes a circular cross-section defining an area less than an area of the cross-section of the proximal end portion of the push member.

In Example 9, the guide extension catheter of any one or any combination of Examples 1-7 can optionally be configured such that an intermediate or distal end portion of the push member includes a cross-section defined by an arcuate first surface, which has the same or substantially the same radius of curvature as the guide catheter's inner wall surface, and an arcuate second surface, which extends from a first end of the first surface to a second end of the first surface.

In Example 10, the guide extension catheter of any one of Examples 7, 8 or 9 can optionally be configured such that the cross-sectional area of the distal end portion of the push member is less than the cross-sectional area of the intermediate portion of the push member.

In Example 11, the guide extension catheter of any one of Examples 7, 8 or 9 can optionally be configured such that a stiffness of the push member's proximal end portion is greater than a stiffness of the push member's intermediate and distal end portions.

In Example 12, the guide extension catheter of any one or any combination of Examples 1-11 can optionally be configured such that the arc length of the first surface is greater than a length of the second surface.

In Example 13, the guide extension catheter of any one or any combination of Examples 1-12 can optionally further comprise one or more bands along the length of the push member to urge it to one side of the guide catheter's inner wall surface.

In Example 14, the guide extension catheter of any one or any combination of Examples 1-13 can optionally be configured such that a diameter of the lumen of the tube member is not more than one French size smaller than a diameter of the lumen of the guide catheter.

In Example 15, the guide extension catheter of any one or any combination of Examples 1-14 can optionally further comprise a concave track defining a partially cylindrical opening leading into the tube member.

In Example 16, the guide extension catheter of Example 15 can optionally be configured such that a first segment of the concave track includes an arcuate cross-sectional shape.

In Example 17, the guide extension catheter of Example 16 can optionally be configured such that a second segment of the concave track includes a hemicylindrical cross-sectional shape.

In Example 18, the guide extension catheter of any one or any combination of Examples 1-14 can optionally be configured such that a proximal end of the tube member is partially or completely radially flared.

In Example 19, the guide extension catheter of any one or any combination of Examples 1-18 can optionally be configured such that a proximal end of the tube member is skived.

In Example 20, a guide extension catheter for use with a guide catheter can comprise an elongate tube member and a lumenless push member eccentrically coupled to the tube member at a distal end portion. The tube member can define a lumen and have an outer diameter smaller than a lumen of the guide catheter. The push member can extend proximally from its point of coupling with the tube member for slidably positioning the tube member within and partially beyond a distal end of the guide catheter. A proximal end portion of the push member can include a cross-section defined by an arcuate first surface, which is configured to engage an inner wall surface of the guide catheter, and an opposing second surface, which is spaced furthest from the first surface as its center point. One or both of an intermediate portion and the distal end portion of the push member can include a cross-section defined by opposing first and second flat surfaces and opposing third and fourth flat surfaces.

In Example 21, the guide extension catheter of Example 20 can optionally be configured such that the proximal end portion of the push member has a proximal stiffness and the distal end portion of the push member has a distal stiffness, which is less than the proximal stiffness.

In Example 22, the guide extension catheter of any one of Examples 20 or 21 can optionally be configured such that the cross-section of the push member's proximal end portion transitions along the length of the push member to the cross-section of the push member's distal end portion.

In Example 23, the guide extension catheter of any one or any combination of Examples 20-22 can optionally be configured such that the proximal end portion has a relatively low flexibility, the distal end portion has a relatively high flexibility, and the intermediate portion has a middle flexibility between that of the relatively low flexibility of the proximal end portion and the relatively high flexibility of the distal end portion.

In Example 24, the guide extension catheter of any one or any combination of Examples 20-23 can optionally be configured such that the cross-section of the push member's proximal end portion is further defined by third and four arcuate surfaces that connect the first and second surfaces.

In Example 25, the guide extension catheter of Example 24 can optionally be configured such that a distance change between center points of the first and second surfaces at the push member's proximal end portion to center points of the first and second surfaces at the push member's intermediate portion is less than a distance change between center points of the third and fourth surfaces at the push member's proximal end portion to center points of the third and fourth surfaces at the push member's intermediate portion.

In Example 26, the guide extension catheter of any one or any combination of Examples 20-25 can optionally be configured such that a distance between center points of the first and second surfaces at the push member's proximal end portion is between 40%-60% of an arc length of the first surface at the push member's proximal end portion.

In Example 27, the guide extension catheter of any one or any combination of Examples 1-26 can optionally be configured such that all components or options recited are available to use or select from.

CLOSING NOTES

The present guide extension catheters and methods can provide support or guidance for an interventional device beyond the distal end of a guide catheter. Additionally, the guide extension catheters can allow for the position of the guide catheter to be maintained relative to an ostium or branch of a target vessel during an interventional procedure. The guide extension catheters include a proximal push member and a distal tube member extendible beyond the distal end of the guide catheter. The configuration of the push member can provide an advantageous blend of stiffness, flexibility and space conservation, such that an operating physician can push the guide extension catheters where desired without kinking or improper bending and without reducing the effective device delivery area through the guide catheter.

The above Detailed Description includes references to the accompanying drawings, which form a part of the Detailed Description. The Detailed Description should be read with reference to the drawings. The drawings show, by way of illustration, specific embodiments in which the present guide extension catheters and related methods can be practiced. These embodiments are also referred to herein as "examples."

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" refers to a range of numbers that one of skill in the art considers equivalent to the recited value (i.e., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to an operating physician. "Distal" and "distally" refer to a position that is distant from, or in a direction away from, the physician. "Proximal" and "proximally" refer to a position that is near, or in a direction toward, the physician. And the term "interventional device(s)" is used to include, but is not limited to, guidewires, balloon catheters, stents and stent catheters.

The scope of the present guide extension catheters and methods should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A guide extension catheter for use with a guide catheter, comprising:
    an elongate tube member defining a lumen and having an outer diameter smaller than a lumen of the guide catheter; and
    a push member eccentrically coupled relative to an axis of the tube member and extending proximal of the tube member for slidably positioning the tube member within and partially beyond a distal end of the guide catheter,
    wherein at least a proximal end portion of the push member includes a cross-section defined by an arcuate first surface, which is configured to engage an inner wall surface of the guide catheter along an arc length defined by a guide catheter central angle of at least 20 degrees, and a flat second surface, which is located opposite the first surface, the second surface having a center point at least 0.010 inches from a center point of the first surface and wherein the center point of the second surface is spaced furthest away from the first surface, and
    wherein an intermediate portion or a distal end portion of the push member includes a rectangular cross-section defining an area less than an area of the cross-section of the proximal end portion of the push member.

2. The guide extension catheter of claim 1, wherein the first surface of the push member's proximal end portion has the same radius of curvature as the guide catheter's inner wall surface.

3. The guide extension catheter of claim 2, wherein the cross-section of the proximal end portion of the push member is further defined by third and fourth arcuate surfaces that connect the first and second surfaces,
    the third and fourth surfaces having a radius of curvature less than the radius of curvature of the first surface.

4. The guide extension catheter of claim 3, wherein the radius of curvature of the first surface is at least three times greater than the radius of curvature of the third and fourth surfaces.

5. The guide extension catheter of claim 1, wherein the push member is solid.

6. The guide extension catheter of claim 1, wherein the arc length of the first surface is greater than a length of the second surface.

7. The guide extension catheter of claim 1, further comprising one or more bands along the length of the push member.

8. The guide extension catheter of claim 1, wherein a diameter of the lumen of the tube member is not more than one French size smaller than a diameter of the lumen of the guide catheter.

9. The guide extension catheter of claim 1, further comprising a concave track defining a partially cylindrical opening leading into the tube member.

10. The guide extension catheter of claim 9, wherein a first segment of the concave track includes an arcuate cross-sectional shape.

11. The guide extension catheter of claim 10, wherein a second segment of the concave track extends circumferentially 40% to 70%, inclusive, of a cross-sectional circumference of the tube member.

12. The guide extension catheter of claim 1, wherein a proximal end of the tube member is at least partially radially flared.

13. The guide extension catheter of claim 1, wherein a proximal end of the tube member is skived.

14. A guide extension catheter for use with a guide catheter, comprising:
    an elongate tube member defining a lumen and having an outer diameter smaller than a lumen of the guide catheter; and
    a lumenless push member eccentrically coupled to the tube member at a distal end portion and extending proximally therefrom to a proximal end portion for slidably positioning the tube member within and partially beyond a distal end of the guide catheter,
    the proximal end portion of the push member including a cross-section defined by an arcuate first surface configured to engage an inner wall surface of the guide catheter, and an opposing flat second surface, the second surface spaced furthest away from the first surface at a center point of the second surface, and
    both an intermediate portion and the distal end portion of the push member including a cross-section defined by opposing first and second surfaces and opposing third and fourth surfaces, each of the surfaces having a flat geometry.

15. The guide extension catheter of claim 14, wherein the proximal end portion of the push member has a proximal stiffness and the distal end portion of the push member has a distal stiffness, which is less than the proximal stiffness.

16. The guide extension catheter of claim 14, wherein the cross-section of the push member's proximal end portion transitions along the length of the push member to the cross-section of the push member's distal end portion.

17. The guide extension catheter of claim 14, wherein the proximal end portion has a first flexibility, the distal end portion has a second flexibility that is higher than the first flexibility, and the intermediate portion has a third flexibility between that of the first flexibility of the proximal end portion and the second flexibility of the distal end portion.

18. The guide extension catheter of claim 14, wherein the cross-section of the push member's proximal end portion is further defined by third and fourth arcuate surfaces that connect the first and second surfaces.

19. The guide extension catheter of claim 18, wherein a distance change between center points of the first and second surfaces at the push member's proximal end portion to center points of the first and second surfaces at the push member's intermediate portion is less than a distance change between center points of the third and fourth surfaces at the push member's proximal end portion to center points of the third and fourth surfaces at the push member's intermediate portion.

20. The guide extension catheter of claim 14, wherein a distance between center points of the first and second surfaces at the push member's proximal end portion is between 40%-60% of an arc length of the first surface at the push member's proximal end portion.

* * * * *

UNITED STATES PATENT AND TRADEMARK OFFICE
CERTIFICATE OF CORRECTION

PATENT NO. : 10,751,514 B2
APPLICATION NO. : 15/581176
DATED : August 25, 2020
INVENTOR(S) : Joshua Brenizer and Dean Peterson Page 1 of 1

It is certified that error appears in the above-identified patent and that said Letters Patent is hereby corrected as shown below:

On the Title Page

Item (71), Line 2, the Applicant's country of residence is incorrect. Please delete "Valletta, MT (US)" and insert --Valletta (MT)--.

Signed and Sealed this
Twenty-second Day of September, 2020

Andrei Iancu
*Director of the United States Patent and Trademark Office*